United States Patent
Baumann et al.

(10) Patent No.: US 6,770,770 B1
(45) Date of Patent: Aug. 3, 2004

(54) PHOSPHITES

(75) Inventors: Robert Baumann, Mannheim (DE); Jakob Fischer, Freising (DE); Tim Jungkamp, Dossenheim (DE); Dagmar Pascale Kunsmann-Keitel, Limburgerhof (DE); Wolfgang Siegel, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 161 days.

(21) Appl. No.: 10/111,477

(22) PCT Filed: Oct. 25, 2000

(86) PCT No.: PCT/EP00/10523

§ 371 (c)(1),
(2), (4) Date: Apr. 25, 2002

(87) PCT Pub. No.: WO01/36429

PCT Pub. Date: May 25, 2001

(30) Foreign Application Priority Data

Nov. 3, 1999 (DE) .......................................... 199 53 058

(51) Int. Cl.$^7$ .......................... C07F 9/145; B01J 31/18; C07C 253/10; C07C 253/30

(52) U.S. Cl. .......................... 556/13; 556/155; 558/332; 558/335; 585/671

(58) Field of Search .................. 556/13, 155; 502/155; 558/332, 335; 585/671

(56) References Cited

U.S. PATENT DOCUMENTS

| | | | | |
|---|---|---|---|---|
| 3,346,608 A | * | 10/1967 | von Kutepow et al. | 556/13 |
| 3,414,629 A | * | 12/1968 | McCall et al. | 585/369 |
| 3,766,237 A | | 10/1973 | Chia et al. | 260/465.3 |
| 3,847,959 A | * | 11/1974 | Shook, Jr. et al. | 556/13 |
| 3,850,973 A | | 11/1974 | Seidel et al. | 260/464 |
| 3,903,120 A | | 9/1975 | Shook et al. | 260/439 R |
| 3,925,445 A | | 12/1975 | King et al. | 260/465 R |
| 4,385,007 A | * | 5/1983 | Shook, Jr. | 558/338 |
| 4,387,056 A | * | 6/1983 | Stowe | 556/13 |

FOREIGN PATENT DOCUMENTS

WO  97/36856  10/1997

OTHER PUBLICATIONS

XP–002161284 Chem. Abstr., vol. 61, No. 1 (1964).

* cited by examiner

Primary Examiner—Porfirio Nazario-Gonzalez

(74) Attorney, Agent, or Firm—Keil & Weinkauf

(57) ABSTRACT

Novel phosphites have the formula I $$P(O-R^1)_x(O-R^2)_y(O-R^3)_z(O-R^4)_p \qquad I$$

where $R^1$: aromatic radical having a $C_1$–$C_{18}$-alkyl substituent in the o position relative to the oxygen atom which connects the phosphorus atom to the aromatic system, or having an aromatic substituent in the o position relative to the oxygen atom which connects the phosphorus atom to the aromatic system, or having an aromatic system fused on in the o position relative to the oxygen atom which connects the phosphorus atom to the aromatic system, $R^2$: aromatic radical having a $C_1$–$C_{18}$-alkyl substituent in the m position relative to the oxygen atom which connects the phosphorus atom to the aromatic system, or having an aromatic substituent in the m position relative to the oxygen atom which connects the phosphorus atom to the aromatic system, or having an aromatic system fused on in the m position relative to the oxygen atom which connects the phosphorus atom to the aromatic system, where the aromatic radical bears a hydrogen atom in the o position relative to the oxygen atom which connects the phosphorus atom to the aromatic system, $R^3$: aromatic radical having a $C_1$–$C_{18}$-alkyl substituent in the p position relative to the oxygen atom which connects the phosphorus atom to the aromatic system, or having an aromatic substituent in the p position relative to the oxygen atom which connects the phosphorus atom to the aromatic system, where the aromatic radical bears a hydrogen atom in the o position relative to the oxygen atom which connects the phosphorus atom to the aromatic system, $R^4$: aromatic radical which bears substituents other than those defined for $R^1$, $R^2$ and $R^3$ in the o, m and p positions relative to the oxygen atom which connects the phosphorus atom to the aromatic system, where the aromatic radical bears a hydrogen atom in the o position relative to the oxygen atom which connects the phosphorus atom to the aromatic system, x: 1 or 2, y, z, p: independently of one another, 0, 1 or 2, with the proviso that x+y+z+p=3.

12 Claims, No Drawings

PHOSPHITES

The present invention relates to novel phosphites, a process for preparing them, their use as ligand in transition metal complexes, novel transition metal complexes, a process for preparing them, their use as catalyst and processes carried out in the presence of such transition metal complexes as catalyst.

Triaryl phosphites, nickel complexes containing such phosphites as ligands and the use of such complexes as catalysts are known.

DE-A 2 237 703, U.S. Pat. No. 3,850,973 and U.S. Pat. No. 3,903,120 describe a process for the hydrocyanation of unsaturated organic compounds and the isomerization of nitriles in the presence of nickel(0) complexes containing tri-o-tolyl phosphite as ligand. A disadvantage of this process is that the stability of such nickel complexes is unsatisfactory. This low stability is reflected in a very low content of Ni(0), which is the active species for the hydrocyanation, in the reaction solution.

U.S. Pat. No. 3,766,237 and U.S. Pat. No. 3,903,120 describe a process for the hydrocyanation of unsaturated organic compounds and the isomerization of nitriles in the presence of nickel(0) complexes containing tri-m/p-tolyl phosphite as ligand. A disadvantage of this process is that the reactivity of such nickel complexes is unsatisfactory.

It is an object of the present invention to provide a process which makes possible the hydrocyanation of unsaturated organic compounds in a technically simple and economical manner using a catalyst which has high stability and high reactivity.

We have found that this object is achieved by phosphites of the formula I

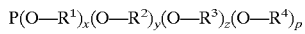
$$P(O-R^1)_x(O-R^2)_y(O-R^3)_z(O-R^4)_p \qquad I$$

where $R^1$: aromatic radical having a $C_1$–$C_{18}$-alkyl substituent in the o position relative to the oxygen atom which connects the phosphorus atom to the aromatic system, or having an aromatic substituent in the o position relative to the oxygen atom which connects the phosphorus atom to the aromatic system, or having an aromatic system fused on in the o position relative to the oxygen atom which connects the phosphorus atom to the aromatic system, $R^2$: aromatic radical having a $C_1$–$C_{18}$-alkyl substituent in the m position relative to the oxygen atom which connects the phosphorus atom to the aromatic system, or having an aromatic substituent in the m position relative to the oxygen atom which connects the phosphorus atom to the aromatic system, or having an aromatic system fused on in the m position relative to the oxygen atom which connects the phosphorus atom to the aromatic system, where the aromatic radical bears a hydrogen atom in the o position relative to the oxygen atom which connects the phosphorus atom to the aromatic system, $R^3$: aromatic radical having a $C_1$–$C_{18}$-alkyl substituent in the p position relative to the oxygen atom which connects the phosphorus atom to the aromatic system, or having an aromatic substituent in the p position relative to the oxygen atom which connects the phosphorus atom to the aromatic system, where the aromatic radical bears a hydrogen atom in the o position relative to the oxygen atom which connects the phosphorus atom to the aromatic system, $R^4$: aromatic radical which bears substituents other than those defined for $R^1$, $R^2$ and $R^3$ in the o, m and p positions relative to the oxygen atom which connects the phosphorus atom to the aromatic system, where the aromatic radical bears a hydrogen atom in the o position relative to the oxygen atom which connects the phosphorus atom to the aromatic system, x: 1 or 2, y, z, p: independently of one another, 0, 1 or 2, with the proviso that x+y+z+p=3, and by a process for preparing them, their use as ligand in transition metal complexes, novel transition metal complexes, a process for preparing them, their use as catalyst and processes carried out in the presence of such transition metal complexes as catalyst.

According to the present invention, the radical $R^1$ is an aromatic radical having a $C_1$–$C_{18}$-alkyl substituent in the o position relative to the oxygen atom which connects the phosphorus atom to the aromatic system, or having an aromatic substituent in the o position relative to the oxygen atom which connects the phosphorus atom to the aromatic system, or having an aromatic system fused on in the o position relative to the oxygen atom which connects the phosphorus atom to the aromatic system.

Suitable aromatic radicals are heterocycles and preferably homocycles such as the phenyl radical.

The aromatic radical may bear further functional groups such as alkoxy groups or halogens, for example chlorine or bromine; the aromatic radical preferably bears no functional groups.

According to the present invention, the aromatic radical bears a $C_1$–$C_{18}$-alkyl substituent in the o position relative to the oxygen atom which connects the phosphorus atom to the aromatic system or has an aromatic system fused on in the o position relative to the oxygen atom which connects the phosphorus atom to the aromatic system. Alkyl radicals which may be present are linear or cyclic $C_1$–$C_{18}$ radicals, preferably $C_1$–$C_9$ radicals such as methyl, ethyl, n-propyl, i-propyl, n-butyl, i-butyl, s-butyl, n-pentyl and its isomers, n-hexyl and its isomers, cyclopentyl or cyclohexyl radicals, where the cyclic alkyl radicals may bear linear or further cyclic alkyl radicals or aromatic radicals as substituents and the alkyl radicals may bear cyclic alkyl radicals or aromatic radicals as substituents. Preferred alkyl radicals are methyl, ethyl, n-propyl, i-propyl, n-butyl, i-butyl and s-butyl.

These alkyl radicals may bear further functional groups such as alkoxy groups, amino groups such as unsubstituted, monosubstituted or disubstituted amino groups, mercapto groups such as substituted mercapto groups, where the substitution may be by the abovementioned alkyl groups or aromatic radicals. The alkyl radicals preferably bear no functional groups.

In the alkyl radicals, carbon atoms may be replaced by other atoms such as oxygen, nitrogen or sulfur; the alkyl radicals preferably have none of their carbon atoms replaced.

Suitable aromatic substituents are heterocycles and preferably homocycles such as the phenyl radical.

The aromatic substituent may bear further functional groups such as alkoxy groups or halogens, for example chlorine or bromine; the aromatic substituent preferably bears no functional groups.

The aromatic substituent may bear one or more $C_1$–$C_{18}$ alkyl substituents or one or more fused-on aromatic systems or be free of further substituents.

Alkyl radicals which may be present are linear or cyclic $C_1$–$C_{18}$ radicals, preferably $C_1$–$C_9$ radicals such as methyl, ethyl, n-propyl, i-propyl, n-butyl, i-butyl, s-butyl, n-pentyl and its isomers, n-hexyl and its isomers, cyclopentyl or cyclohexyl radicals, where the cyclic alkyl radicals may bear linear or further cyclic alkyl radicals or aromatic radicals as substituents and the alkyl radicals may bear cyclic alkyl radicals or aromatic radicals as substituents. Preferred alkyl radicals are methyl, ethyl, n-propyl, i-propyl, n-butyl, i-butyl and s-butyl.

These alkyl radicals may bear further functional groups such as alkoxy groups, amino groups such as unsubstituted, monosubstituted or disubstituted amino groups, mercapto groups such as substituted mercapto groups, where the substitution may be by the abovementioned alkyl groups or aromatic radicals. The alkyl radicals preferably bear no functional groups.

In the alkyl radicals, carbon atoms may be replaced by other atoms such as oxygen, nitrogen or sulfur; the alkyl radicals preferably have none of their carbon atoms replaced.

The radical $R^1$ is advantageously o-tolyl, o-ethylphenyl, o-n-propylphenyl, o-isopropylphenyl, o-n-butylphenyl, o-sec-butylphenyl, o-tert-butylphenyl, (o-phenyl)phenyl or 1-naphthyl.

According to the present invention, $R^2$ is an aromatic radical having a $C_1$–$C_{18}$-alkyl substituent in the m position relative to the oxygen atom which connects the phosphorus atom to the aromatic system, or having an aromatic substituent in the m position relative to the oxygen atom which connects the phosphorus atom to the aromatic system, or having an aromatic system fused on in the m position relative to the oxygen atom which connects the phosphorus atom to the aromatic system, where the aromatic radical bears a hydrogen atom in the o position relative to the oxygen atom which connects the phosphorus atom to the aromatic system.

Suitable aromatic radicals are heterocycles and preferably homocycles such as the phenyl radical.

The aromatic radical may bear further functional groups such as alkoxy groups or halogens, for example chlorine or bromine; the aromatic radical preferably bears no functional groups.

According to the present invention, the aromatic radical bears a $C_1$–$C_{18}$-alkyl substituent in the m position relative to the oxygen atom which connects the phosphorus atom to the aromatic system or has an aromatic system fused on in the m position relative to the oxygen atom which connects the phosphorus atom to the aromatic system. Alkyl radicals which may be present are linear or cyclic $C_1$–$C_{18}$ radicals, preferably $C_1$–$C_9$ radicals such as methyl, ethyl, n-propyl, i-propyl, n-butyl, i-butyl, s-butyl, n-pentyl and its isomers, n-hexyl and its isomers, cyclopentyl or cyclohexyl radicals, where the cyclic alkyl radicals may bear linear or further cyclic alkyl radicals or aromatic radicals as substituents and the alkyl radicals may bear cyclic alkyl radicals or aromatic radicals as substituents. Preferred alkyl radicals are methyl, ethyl, n-propyl, i-propyl, n-butyl, i-butyl and s-butyl.

These alkyl radicals may bear further functional groups such as alkoxy groups, amino groups such as unsubstituted, monosubstituted or disubstituted amino groups, mercapto groups such as substituted mercapto groups, where substitution may be by the abovementioned alkyl groups or aromatic radicals. The alkyl radicals preferably bear no functional groups.

In the alkyl radicals, carbon atoms may be replaced by other atoms such as oxygen, nitrogen or sulfur; the alkyl radicals preferably have none of their carbon atoms replaced.

Suitable aromatic substituents are heterocycles and preferably homocycles such as the phenyl radical.

The aromatic substituent may bear further functional groups such as alkoxy groups or halogens, for example chlorine or bromine; the aromatic substituent preferably bears no functional groups.

The aromatic substituent may bear one or more $C_1$–$C_{18}$-alkyl substituents or one or more fused-on aromatic systems or be free of further substituents.

The alkyl radicals may be linear or cyclic $C_1$–$C_{18}$ radicals, preferably $C_1$–$C_9$ radicals such as methyl, ethyl, n-propyl, i-propyl, n-butyl, i-butyl, s-butyl, n-pentyl and its isomers, n-hexyl and its isomers, cyclopentyl or cyclohexyl radicals, where the cyclic alkyl radicals may bear linear or further cyclic alkyl radicals or aromatic radicals as substituents and the alkyl radicals may bear cyclic alkyl radicals or aromatic radicals as substituents. Preferred alkyl radicals are methyl, ethyl, n-propyl, i-propyl, n-butyl, i-butyl and s-butyl.

These alkyl radicals may bear further functional groups such as alkoxy groups, amino groups such as unsubstituted, monosubstituted or disubstituted amino groups, mercapto groups such as substituted mercapto groups, where substitution may be by the abovementioned alkyl groups or aromatic radicals. The alkyl radicals preferably bear no functional groups.

In the alkyl radicals, carbon atoms may be replaced by other atoms such as oxygen, nitrogen or sulfur; the alkyl radicals preferably have none of their carbon atoms replaced.

The radical $R^2$ is advantageously m-tolyl, m-ethylphenyl, m-n-propylphenyl, m-isopropylphenyl, m-n-butylphenyl, m-sec-butylphenyl, m-tert-butylphenyl, (m-phenyl)phenyl or 2-naphthyl.

According to the present invention, the radical $R^3$ is an aromatic radical having a $C_1$–$C_{18}$-alkyl substituent in the p position relative to the oxygen atom which connects the phosphorus atom to the aromatic system, or having an aromatic substituent in the p position relative to the oxygen atom which connects the phosphorus atom to the aromatic system, where the aromatic radical bears a hydrogen atom in the o position relative to the oxygen atom which connects the phosphorus atom to the aromatic system.

Suitable aromatic radicals are heterocycles and preferably homocycles such as the phenyl radical.

The aromatic radical may bear further functional groups such as alkoxy groups or halogens, for example chlorine or bromine; the aromatic radical preferably bears no functional groups.

According to the present invention, the aromatic radical bears a $C_1$–$C_{18}$-alkyl substituent in the p position relative to the oxygen atom which connects the phosphorus atom to the aromatic system or has an aromatic system fused on in the p position relative to the oxygen atom which connects the phosphorus atom to the aromatic system. Alkyl radicals which may be present are linear or cyclic $C_1$–$C_{18}$ radicals, preferably $C_1$–$C_9$ radicals such as methyl, ethyl, n-propyl, i-propyl, n-butyl, i-butyl, s-butyl, n-pentyl and its isomers, n-hexyl and its isomers, cyclopentyl or cyclohexyl radicals, where the cyclic alkyl radicals may bear linear or further cyclic alkyl radicals or aromatic radicals as substituents and the alkyl radicals may bear cyclic alkyl radicals or aromatic radicals as substituents. Preferred alkyl radicals are methyl, ethyl, n-propyl, i-propyl, n-butyl, i-butyl and s-butyl.

These alkyl radicals may bear further functional groups such as alkoxy groups, amino groups such as unsubstituted, monosubstituted or disubstituted amino groups, mercapto groups such as substituted mercapto groups, where substitution may be by the abovementioned alkyl groups or aromatic radicals. The alkyl radicals preferably bear no functional groups.

In the alkyl radicals, carbon atoms may be replaced by other atoms such as oxygen, nitrogen or sulfur; the alkyl radicals preferably have none of their carbon atoms replaced.

Suitable aromatic substituents are heterocycles and preferably homocycles such as the phenyl radical.

The aromatic substituent may bear further functional groups such as alkoxy groups or halogens, for example chlorine or bromine; the aromatic substituent preferably bears no functional groups.

The aromatic substituent may bear one or more $C_1$–$C_{18}$-alkyl substituents or one or more fused-on aromatic systems or be free of further substituents.

Alkyl radicals which may be present are linear or cyclic $C_1$–$C_{18}$ radicals, preferably $C_1$–$C_9$ radicals such as methyl, ethyl, n-propyl, i-propyl, n-butyl, i-butyl, s-butyl, n-pentyl and its isomers, n-hexyl and its isomers, cyclopentyl or cyclohexyl radicals, where the cyclic alkyl radicals may bear linear or further cyclic alkyl radicals or aromatic radicals as substituents and the alkyl radicals may bear cyclic alkyl radicals or aromatic radicals as substituents. Preferred alkyl radicals are methyl, ethyl, n-propyl, i-propyl, n-butyl, i-butyl and s-butyl.

These alkyl radicals may bear further functional groups such as alkoxy groups, amino groups such as unsubstituted, monosubstituted or disubstituted amino groups, mercapto groups such as substituted mercapto groups, where substitution may be by the abovementioned alkyl groups or aromatic radicals. The alkyl radicals preferably bear no functional groups.

In the alkyl radicals, carbon atoms may be replaced by other atoms such as oxygen, nitrogen or sulfur; the alkyl radicals preferably have none of their carbon atoms replaced.

The radical $R^3$ is advantageously p-tolyl, p-ethylphenyl, p-n-propylphenyl, p-isopropylphenyl, p-n-butylphenyl, p-sec-butylphenyl, p-tert-butylphenyl or (p-phenyl)phenyl.

According to the present invention, the radical $R^4$ is an aromatic radical which bears substituents other than those defined for $R^1$, $R^2$ and $R^3$ in the o, m and p positions relative to the oxygen atom which connects the phosphorus atom to the aromatic system, where the aromatic radical bears a hydrogen atom in the o position relative to the oxygen atom which connects the phosphorus atom to the aromatic system.

The aromatic radical may bear functional groups such as alkoxy groups or halogens, for example chlorine or bromine; the aromatic radical preferably bears no functional groups.

As radical $R^4$, preference is given to the phenyl radical.

Among the radicals $R^1$, $R^2$, $R^3$ or $R^4$, two or three radicals in the formula I can be linked to one another either via $C_1$–$C_{18}$-alkylene groups or directly.

Possible alkylene groups are linear or cyclic $C_1$–$C_{18}$ radicals, preferably $C_1$–$C_9$ radicals such as methylene, ethylene, n-propylene, n-butylene, n-pentylene and its isomers, n-hexylene and its isomers, cyclopentylene or cyclohexylene radicals, where the cyclic alkylene radicals may bear linear or further cyclic alkyl radicals or aromatic radicals as substituents and the alkylene radicals may bear cyclic alkyl radicals or aromatic radicals as substituents, for example as in 1-methylethylene, 1,1-dimethylethylene, 1,2-dimethylethylene, 1-methyl-n-propylene, 2-methyl-n-propylene, 1,1-dimethyl-n-propylene, 1,2-dimethyl-n-propylene, 1,3-dimethyl-n-propylene, 2,2-dimethyl-n-propylene radicals.

The alkylene radicals may bear further functional groups such as alkoxy groups, amino groups such as unsubstituted, monosubstituted or disubstituted amino groups, mercapto groups such as substituted mercapto groups, where substitution may be by the alkyl groups nominated in the definition of $R^1$, $R^2$ or $R^3$ or aromatic radicals. The alkyl radicals preferably bear no functional groups.

In the alkylene radicals, carbon atoms may be replaced by other atoms such as oxygen, nitrogen or sulfur; the alkylene radicals preferably have none of their carbon atoms replaced.

According to the present invention, the index x is 1 or 2.

According to the present invention, the indices y, z and p are, independently of one another, 0, 1 or 2, with the proviso that the sum of the indices x, y, z and p, i.e. x+y+z+p, is 3.

p is preferably 0.

This gives the following possibilities for the indices x, y, z and p in accordance with the present invention:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Particularly preferred phosphites are those in which $R^1$ is the o-isopropylphenyl radical, $R^2$ is the m-tolyl radical and $R^3$ is the p-tolyl radical and the indices are as shown in the table, those in which $R^1$ is the o-tolyl radical, $R^2$ is the m-tolyl radical and $R^3$ is the p-tolyl radical and the indices are as shown in the table, those in which $R^1$ is the 1-naphthyl radical, $R^2$ is the m-tolyl radical and $R^3$ is the p-tolyl radical and the indices are as shown in the table, those in which $R^1$ is the o-tolyl radical, $R^2$ is the 2-naphthyl radical and $R^3$ is the p-tolyl radical and the indices are as shown in the table, those in which $R^1$ is the o-isopropylphenyl radical, $R^2$ is the 2-naphthyl radical and $R^3$ is the p-tolyl radical and the indices are as shown in the table and also mixtures of these phosphites.

Phosphites of the formula I can be obtained by a) reacting a phosphorus trihalide with an alcohol selected from the group consisting of $R^1OH$, $R^2OH$, $R^3OH$ and $R^4OH$ and mixtures thereof to give a dihalophosphorous monoester, b) reacting this dihalophosphorous monoester with an alcohol selected from the group consisting of $R^1OH$, $R^2OH$, $R^3OH$ and $R^4OH$ and mixtures thereof to give a monohalophosphorous diester and c) reacting this monohalophosphorous diester with an alcohol selected from the group consisting of $R^1OH$, $R^2OH$, $R^3OH$ and $R^4OH$ and mixtures thereof to give a phosphite of the formula I.

The reaction can be carried out in three separate steps.

It is possible to combine two of the three steps, i.e. a with b or b with c.

It is also possible to combine all of the steps a, b and c with one another.

In carrying out the reaction, suitable parameters and amounts of alcohol selected from the group consisting of $R^1OH$, $R^2OH$, $R^3OH$ and $R^4OH$ and mixtures thereof can easily be determined by a few simple preliminary experiments.

As phosphorus trihalide, it is in principle possible to use any phosphorus trihalide, preferably one in which the halide is Cl, Br, I, in particular Cl, or mixtures thereof. It is also possible to use mixtures of various identically or differently halogen-substituted phosphines as phosphorus trihalide. Particular preference is given to $PCl_3$.

In steps a, b and c, the reaction can advantageously be carried out at temperatures in the range from 10 to 200° C., preferably from 50 to 150° C., in particular from 70 to 120° C.

In steps a, b and c, preference is given to using a molar ratio of halide radicals used in the respective step to hydroxyl groups of the alcohols used of from 1:10 to 10:1, preferably from 1:3 to 3:1.

The reaction in steps a, b and c can be carried out in the presence of an inorganic or organic, in particular liquid, diluent such as an ester, for example ethyl acetate, an ether, for example methyl-t-butyl ether, diethyl ether, dioxane, or tetrahydrofuran, an aromatic compound, for example toluene, or a halogenated hydrocarbon, for example tetrachloromethane, chloroform, methylene chloride, or a mixture of such diluents.

The reaction is preferably carried out without using such an inorganic or organic diluent.

The hydrogen halide formed in the reaction, which is usually obtained in gaseous form under the reaction conditions, can advantageously be separated off and passed to chemical processes known per se.

The steps a, b and c usually give mixtures in which the desired component is present.

The desired component can be separated off in a manner known per se, for example by extraction or distillation, preferably by distillation.

If the separation is carried out by distillation, reduction of the pressure to below ambient pressure has been found to be advantageous.

The distillation can advantageously be carried out in a column, for example with a side offtake, or in a plurality of columns, e.g. two, three or four columns.

Columns which can be used are columns known per se, for example bubble cap tray columns, sieve tray columns or packed columns.

The optimum process conditions for separating off the phosphites of the formula I can in each case easily be determined by a few simple preliminary experiments.

The phosphites of the formula I can be used as ligands in transition metal complexes.

Transition metals used are advantageously the metals of transition groups I and II and VI to VIII of the Periodic Table, preferably transition group VIII of the Periodic Table, particularly preferably iron, cobalt and nickel, in particular nickel.

If nickel is used, it can be present in various oxidation states such as 0, +1, +2 or +3. Preference is given to nickel(0) and nickel(+2), in particular nickel(0).

To prepare the transition metal complexes, a chemical compound containing a transition metal or preferably a transition metal can be reacted with a phosphite of the formula I. As phosphite of the formula I, it is possible to use a single phosphite of the formula I or a mixture of a plurality of phosphites of the formula I.

The transition metal can be obtained from suitable chemical compounds prior to the reaction, for example from salts such as chlorides by reduction with base metals such as zinc.

If a compound containing a transition metal is used for preparing the transition metal complexes, it is advantageous to employ salts such as chlorides, bromides, acetylacetonates, sulfates and nitrates, for example nickel(2) chloride.

After the reaction of the compound containing a transition metal or of the transition metal with a phosphite of the formula I, the oxidation state of the transition metal in the complex can be changed by means of suitable oxidizing or reducing agents, for example base metals such as zinc, or hydrogen in chemically bound form, e.g. sodium borohydride, or in molecular form, or by electrochemical means.

In the transition metal complexes, the molar ratio of transition metal to phosphite of the formula I can be in the range from 1 to 6, preferably from 2 to 5, in particular 2, 3 or 4.

The transition metal complexes may be free of ligands other than the phosphites of the formula I.

On the other hand, the transition metal complexes may contain further ligands, for example nitrites such as acetonitrile, adiponitrile, 3-pentenenitrile, 4-pentenenitrile or 2-methyl-3-butenenitrile, or olefins such as butadiene, in addition to the phosphites of the formula I.

The preparation of such transition metal complexes can essentially be carried out by methods described in the literature, for example in DE-A-2 237 703, U.S. Pat. No. 3,850,973, U.S. Pat. No. 3,766,237 or U.S. Pat. No. 3,903,120, for preparing transition metal complexes containing tri-o-tolyl phosphite, tri-m-tolyl phosphite or tri-p-tolyl phosphite, using the novel phosphites of the formula I in place of some or all of these tritolyl phosphites.

The transition metal complexes of the present invention can be used as catalysts, in particular as homogeneous catalysts.

It has been found to be particularly advantageous to use the transition metal complexes of the present invention as catalysts in the addition of hydrocyanic acid onto olefinic double bonds, in particular ones which are conjugated with a further olefinic double bond, for example the addition onto butadiene to give a mixture comprising 2-methyl-3-butenenitrile and 3-pentenenitrile. Another similarly advantageous application is the use as catalysts in the addition of hydrocyanic acid onto olefinic double bonds which are not conjugated with a further olefinic double bond, for example addition onto 3-pentenenitrile or 4-pentenenitrile or mixtures thereof, preferably 3-pentenenitrile, to give adiponitrile, or onto 3-pentenoic esters or 4-pentenoic esters or mixtures thereof, preferably 3-pentenoic esters, to give 5-cyanovaleric esters.

It has likewise been found to be particularly advantageous to use the transition metal complexes of the present invention as catalysts in the isomerization of organic nitriles, particularly those in which the nitrile group is not conjugated with an olefinic double bond, for example isomerization of 2-methyl-3-butenenitrile to give 3-pentenenitrile. Another similarly advantageous application is the use as catalysts in the isomerization of organic nitrites in which the nitrile group is conjugated with an olefinic double bond.

Processes for the addition of hydrocyanic acid onto an olefinic double bond or for the isomerization of organic nitrites can in principle be carried out by methods described in the literature which make use of transition metal complexes containing tri-o-tolyl phosphite, tri-m-tolyl phosphite or tri-p-tolyl phosphite, by replacing some or all of these phosphites by the novel phosphites of the formula I.

In these processes, the transition metal complexes of the present invention have a higher stability than those containing tri-o-tolyl phosphite as ligand and a higher reactivity than those containing tri-m/p-tolyl phosphite as ligand.

EXAMPLES

Example 1

A solution of ClP(O-m-tol)$_2$ (298 g, 1.06 mol) in n-hexane (2.5 l) was cooled to 0° C. (ice bath). From two dropping funnels, triethylamine (118 g, 1.17 mol) and o-cresol (114.5 g, 1.06 mol) were added in parallel at 0–5° C. over a period of 2 hours. The reaction mixture was stirred at room temperature for 12 hours. The NEt$_3$.HCl which precipitated was filtered off on a pressure filter and washed with n-hexane (250 ml). This procedure was repeated on a similar scale (1.015 mol). Both crude solutions were combined and filtered through a column filled with Al$_2$O$_3$ to remove residual amounts of chlorine. After evaporation on a rotary evaporator (16 mbar, 50° C.), P(O-m-tol)$_2$(O-o-tol) (L1) was obtained as a yellow oil; yield: 695 g (1.97 mol, 95%); GC 95.6%. Analysis: calc. for C$_{21}$H$_{21}$O$_3$P: C 71.61; H 5.96; P 8.79; found: C 71.6; H 6.0; P 8.8. $^1$H NMR (CDCl$_3$)δ 7.20–6.85 (m, 12), 2.24 (s, 6, C$_6$H$_4$-m-CH$_3$), 2.21 (s, 3, C$_6$H$_4$-o-CH$_3$). $^{13}$C NMR (CDCl$_3$)δ 151.6, 150.2, 139.7, 131.3, 129.7, 129.3, 126.8, 124.9, 124.1, 121.4, 120.2, 117.7, 21.2, 16.7. $^{31}$P NMR (CDCl$_3$)δ 129.7.

Examples 2–9

The ligands L2–L9 were prepared by a method analogous to that for L1, and the results are summarized in Table 1.

TABLE 1

Examples 2–9

| Example | Starting materials | Ligand | Yield (%) | $^{31}$P NMRδ (CDCl$_3$) |
|---|---|---|---|---|
| 2 | ClP(O-m-tol)$_2$, 2-ethylphenol | P(O-m-tol)$_2$(O-o-Et-C$_6$H$_4$)L2 | 98 | 129.6 |
| 3 | ClP(O-m-tol)$_2$, 2-isopropylphenol | P(O-m-tol)$_2$(O-o-iPr-C$_6$H$_4$)L3 | 94 | 130.1 |
| 4 | ClP(O-m-tol)$_2$, 2-sec-butylphenol | P(O-m-tol)$_2$(O-o-secBu-C$_6$H$_4$)L4 | 94 | 129.8 |
| 5 | ClP(O-m-tol)$_2$, 2-tert-butylphenol | P(O-m-tol)$_2$(O-o-tBu-C$_6$H$_4$)L5 | 96 | 129.6 |
| 6 | ClP(O-m-tol)$_2$, 2-phenylphenol | P(O-m-tol)$_2$(O-o-Ph-C$_6$H$_4$)L6 | 80 | 129.5 |
| 7 | ClP(O-m-tol)$_2$, ortho-cresol | P(O-m-tol)$_2$(O-o-tol)$_2$L7 | 95 | 130.6 |
| 8 | ClP(o-m-tol)$_2$, 2,6-dimethylphenol | P(O-m-tol)$_2$(O-2,6Me$_2$-C$_6$H$_3$)L8 | 87 | 134.1 |
| 9 | ClP(O-m-tol)$_2$, 1-naphthol | P(O-m-tol)$_2$(O-1-C$_{10}$H$_7$)L9 | 70 | 129.1 |

Examples 10–12

A mixture of m-cresol, p-cresol and o-isopropylphenol corresponding to the molar composition in Table 2 (18 mol altogether) was placed in a 4 l four-neck flask. The mixture was heated to 70° C. under inert gas. PCl$_3$ (824 g, 6 mol) was added dropwise over a period of 5 hours. The HCl formed was disposed of via a scrubbing tower. The temperature was increased to 110° C. A gentle stream of nitrogen was passed through the reaction mixture while continuing to stir until HCl evolution had stopped.

TABLE 2

Examples 10–12

| | | Starting materials (mol %) | | |
|---|---|---|---|---|
| Example | Product | o-Isopropyl-phenol | m-Cresol | p-Cresol |
| 10 | L10 | 20 | 53 | 27 |
| 11 | L11 | 33 | 45 | 22 |
| 12 | L12 | 40 | 40 | 20 |

Example 13

Ligand L1 from Example 1 (378.3 g, 3-pentenenitrile (99.6 g), nickel powder (29.8 g) and ClP(O-m-tol)$_2$ (1.51 g) were stirred at 95° C. under inert gas for 25 hours. After cooling to room temperature, excess nickel powder was filtered off. The filtrate contained 1.65% by weight of Ni(0). The filtrate was diluted with 3-pentenenitrile and additional ligand to a ligand: nickel(0) ratio 18:1 and a nickel(0) concentration of 0.8% by weight. This solution was used as catalyst solution (C1) in Example 19.

Example 14

Ligand L2 from Example 2 (135.5 g), 3-pentenenitrile (36 g), nickel powder (10 g), ClP(O-m-tol)$_2$ (0.5 g) and PCl$_3$ (6 drops) were stirred at 95° C. under inert gas for 24 hours. After cooling to room temperature, excess nickel powder was filtered off. The filtrate contained 1.55% by weight of Ni(0). The filtrate was diluted with 3-pentenenitrile and additional ligand to a ligand:nickel(0) ratio of 18:1 and a nickel(0) concentration of 0.7% by weight. This solution was used as catalyst solution (C2) in Example 20.

Example 15

Ligand L3 from Example 3 (358.4 g), 3-pentenenitrile (94.4 g), nickel powder (28.2 g) and ClP(O-m-tol)$_2$ (1.43 g) were stirred at 95° C. under inert gas for 25 hours. After cooling to room temperature, excess nickel powder was filtered off. The filtrate contained 1.28% by weight of Ni(0). The filtrate was diluted with 3-pentenenitrile and additional ligand to a ligand:nickel(0) ratio of 18:1 and a nickel(0) concentration of 0.7% by weight. This solution was used as catalyst solution (C3) in Example 21.

Example 16

Ligand L10 from Example 10 (780 g), 3-pentenenitrile (206 g), nickel powder (60 g), ClP(O-m-tol)$_2$ (3.3 g) and PCl$_3$ (35 drops) were stirred at 95° C. under inert gas for 21 hours. After cooling to room temperature, excess nickel powder was filtered off. The filtrate contained 1.5% by weight of Ni(0). The filtrate was diluted with 3-pentenenitrile and additional ligand to a ligand:nickel(0) ratio of 18:1 and a nickel(0) concentration of 10 0.7% by weight. This solution was used as catalyst solution (C4) in Example 22.

Example 17

Ligand L11 from Example 11 (780 g), 3-pentenenitrile (206 g), nickel powder (60 g), ClP(O-m-tol)$_2$ (3.3 g) and PCl$_3$ (35 drops) were stirred at 95° C. under inert gas for 29 hours. After cooling to room temperature, excess nickel powder was filtered off. The filtrate contained 1.1% by weight of Ni(0). The filtrate was diluted with 3-pentenenitrile and additional ligand to a ligand:nickel(0) ratio of 18:1 and a nickel(0) concentration of 0.7% by weight. This solution was used as catalyst solution (C5) in Example 23.

Example 18

Ligand L12 from Example 12 (500 g), 3-pentenenitrile (132 g), nickel powder (40 g), ClP(O-m-tol)$_2$ (2.1 g) and PCl$_3$ (23 drops) were stirred at 95° C. under inert gas for 23 hours. A sample contained 0.72% by weight of Ni(0). A further 20 g of nickel powder and 1 g of ClP(O-m-tol)$_2$ were added, and the mixture was stirred for another 18 hours at 95° C. After cooling to room temperature, excess nickel powder was filtered off. The filtrate contained 0.77% by weight of Ni(0). The filtrate was diluted with 3-pentenenitrile and additional ligand to a ligand:nickel(0) ratio of 18:1 and a nickel(0) concentration of 0.6% by weight. This solution was used as catalyst solution (C6) in Example 24.

Examples 19–25

50 mmol of 2-methyl-3-butenenitrile (2M3BN) were in each case reacted with catalyst solution C1–6 from Examples 13–18 (0.2 mmol of Ni) at 130° C. for 2 hours. To avoid decomposition processes caused by air and moisture, the reactions were carried out in a closed system. Conversion and selectivity were determined by GC after the reaction was complete. For comparison, the procedure was repeated using a solution of the Ni(m-/p-tolyl phosphite) complex (m/p-tolyl phosphite:Ni=18:1, 0.7% by weight of Ni(0), preparation of the solution of the complex analogous to C1–6 from m/p-tolyl phosphite and nickel powder in the presence of 3-pentenenitrile) under identical conditions (50 mmol of 2M3BN, 0.2 mmol of Ni, 130° C., 2 h) (Example 25).

TABLE 3

Examples 19–25

| Example | Catalyst solution | Conversion (%) | Selectivity (c/t-3PN in %) |
|---|---|---|---|
| 19 | C1 | 58.4 | 88.2 |
| 20 | C2 | 70.0 | 94.2 |
| 21 | C3 | 81.7 | 92.4 |
| 22 | C4 | 29.0 | 95.7 |
| 23 | C5 | 56.0 | 97.7 |
| 24 | C6 | 78.3 | 97.8 |
| 25 | Ni (m/p-tolyl phosphite) without ZnCl$_2$ | 7.9 | 81.7 |

We claim:

1. A process for preparing transition metal complexes which comprises reacting Ni(O) or a chemical compound containing Ni(O) with a phosphite of the formula I $$P(O-R^1)_x(O-R^2)_y(O-R^3)_z(O-R^4)_p \qquad I$$

where $R^1$: aromatic radical having a $C_1$–$C_{18}$-alkyl substituent in the o position relative to the oxygen atom which connects the phosphorus atom to the aromatic system, or having an aromatic substituent in the o position relative to the oxygen atom which connects the phosphorus atom to the aromatic system, or having an aromatic system fused on in the o position relative to the oxygen atom which connects the phosphorus atom to the aromatic system, $R^2$: aromatic radical having a $C_1$–$C_{18}$-alkyl substituent in the m position relative to the oxygen atom which connects the phosphorus atom to the aromatic system, or having an aromatic substituent in the m position relative to the oxygen atom which connects the phosphorus atom to the aromatic system, or having an aromatic system fused on in the m position relative to the oxygen atom which connects the phosphorus atom to the aromatic system, where the aromatic radical bears a hydrogen atom in the o position relative to the oxygen atom which connects the phosphorus atom to the aromatic system, $R^3$: aromatic radical having a $C_1$–$C_{18}$-alkyl substituent in the p position relative to the oxygen atom which connects the phosphorus atom to the aromatic system, or having an aromatic substituent in the p position relative to the oxygen atom which connects the phosphorus atom to the aromatic system, where the aromatic radical bears a hydrogen atom in the o position relative to the oxygen atom which connects the phosphorus atom to the aromatic system, $R^4$: aromatic radical which bears substituents other than those defined for $R^1$, $R^2$ and $R^3$ in the o, m and p positions relative to the oxygen atom which connects the phosphorus atom to the aromatic system, where the aromatic radical bears a hydrogen atom in the o position relative to the oxygen atom which connects the phosphorus atom to the aromatic system, x: 1 or 2, y, z, p: independently of one another, 0, 1 or 2, with the proviso that x+y+z+p=3.

2. A process as claimed in claim 1 using a phosphite of the formula I as claimed in claim 1 in which p=0.

3. A process as claimed in claim 1 using a phosphite of the formula I, wherein the radicals $R^1$, $R^2$, $R^3$ and $R^4$ are selected independently of one another from the group consisting of the naphthyl radical, the unsubstituted phenyl radical and phenyl radicals substituted as specified in claim 1.

4. A phosphite of the formula I as claimed in claim 1, wherein the radicals $R^1$, $R^2$, $R^3$ and $R^4$ are substituted or unsubstituted phenyl radicals.

5. A transition metal complex as claimed in claim 1.

6. The method of catalyzing a reaction comprising reacting Ni(O) or a chemical compound containing Ni(O) with a phosphite of the formula 1, wherein $R^1$, $R^2$, $R^3$, $R^4$, x, y, z and p are defined as in claim 1.

7. The method of catalyzing a reaction comprising adding hydrocyanic acid onto an olefinic double bond wherein Ni(O) or a chemical compound containing Ni(O) is reacted with a phosphite of the formula I, wherein $R^1$, $R^2$, $R^3$, $R^4$, x, y, z and p of formula I are defined as in claim 1.

8. The method of catalyzing a reaction comprising isomerizing organic nitriles wherein Ni(O) or a chemical compound containing Ni(O) is reacted with a phosphite of the formula I, wherein $R^1$, $R^2$, $R^3$, $R^4$, x, y, z and p of formula I are defined as in claim 1.

9. A process for the addition of hydrocyanic acid onto an olefinic double bond in the presence of a transition metal complex as claimed in claim 5 as catalyst.

10. A process as claimed in claim 9, wherein hydrocyanic acid is added onto butadiene to give a compound selected from the group consisting of 2-methyl-3-butenenitrile and 3-pentenenitrile.

11. A process for the isomerization of organic nitriles in the presence of a transition metal complex as claimed in claim 5 as catalyst.

12. A process as claimed in claim 11, wherein 2-methyl-3-butenenitrile is isomerized to 3-pentenenitrile.

* * * * *